United States Patent [19]

Angerbauer

[11] Patent Number: 4,709,023
[45] Date of Patent: Nov. 24, 1987

[54] PROCESS FOR THE PREPARATION OF 7-AMINO-3-(3-FORMAMIDOPYRIDINIUM)-METHYL-3-CEPHEM-4-CARBOXYLATE, AND ITS USE FOR THE SYNTHESIS OF β-LACTAM ANTIBIOTICS

[75] Inventor: Rolf Angerbauer, Wuppertal, Fed. Rep. of Germany

[73] Assignee: Bayer Aktiengesellschaft, Leverkusen, Fed. Rep. of Germany

[21] Appl. No.: 730,980

[22] Filed: May 6, 1985

[30] Foreign Application Priority Data

May 22, 1984 [DE] Fed. Rep. of Germany ....... 3419014

[51] Int. Cl.[4] .................. C07D 501/18; A61K 31/545
[52] U.S. Cl. ..................................... 540/224; 514/203; 435/119
[58] Field of Search ............................ 544/25, 26, 27; 540/224; 435/119; 514/203

[56] References Cited

U.S. PATENT DOCUMENTS

| | | | |
|---|---|---|---|
| 4,369,313 | 1/1983 | Jones et al. | 540/224 |
| 4,374,983 | 2/1983 | Robinson | 540/224 |
| 4,407,798 | 10/1983 | Kamiya et al. | 544/25 |
| 4,433,141 | 2/1984 | Jones et al. | 540/225 |

FOREIGN PATENT DOCUMENTS

| | | | |
|---|---|---|---|
| 0042154 | 12/1981 | European Pat. Off. | 137/625.25 |
| 0046964 | 3/1982 | European Pat. Off. | 256/31 |
| 0074645 | 3/1983 | European Pat. Off. | 36/44 |

*Primary Examiner*—Nicholas S. Rizzo
*Attorney, Agent, or Firm*—Sprung Horn Kramer & Woods

[57] ABSTRACT

7-Amino-3-(3-formamidopyridinium)methyl-3-cephem-4-carboxylate of the formula

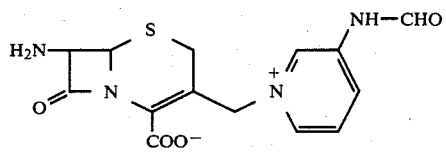

is produced by (a) reacting a compound of the formula

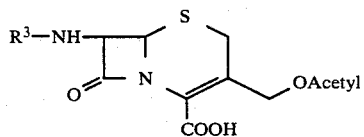

in which
  $R^3$ is a phenacetyl or a thienylacetyl group,
with 3-formamidopyridine to give the compound of the formula

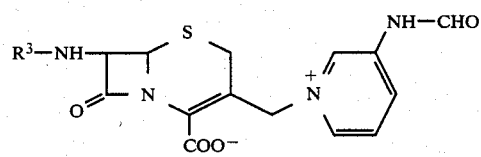

and (b) splitting off the $R^3$ radical.

The product can then be coupled to a suitable acid to produce a cephalosporin and the formyl radical may be split off.

5 Claims, No Drawings

PROCESS FOR THE PREPARATION OF 7-AMINO-3-(3-FORMAMIDOPYRIDINIUM)-METHYL-3-CEPHEM-4-CARBOXYLATE, AND ITS USE FOR THE SYNTHESIS OF β-LACTAM ANTIBIOTICS

The invention relates to a process for the preparation of 7-amino-3-(3-formamidopyridinium)methyl-3-cephem-4-carboxylate of the formula (I)

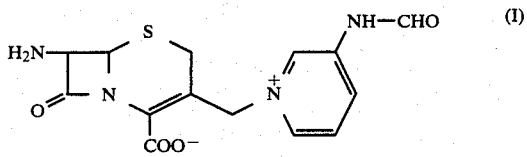

and its use for the synthesis of β-lactam antibiotics of the formula (II)

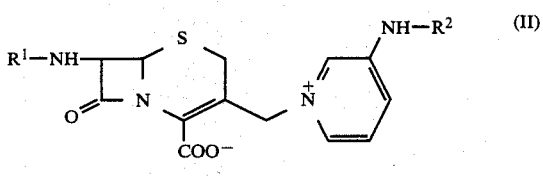

in which
$R^1$ denotes a side chain customary in β-lactam chemistry and
$R^2$ denotes formyl or H.

The compound of the formula (I) is prepared by a process in which a compound of the formula (III)

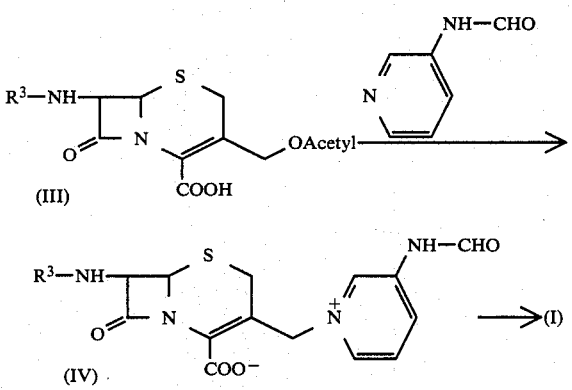

in which
$R^3$ denotes a phenacetyl or a thienylacetyl group,
is reacted with 3-formamidopyridine to give a compound of the formula (IV) from which the compound of the formula (I) is obtained by splitting off the amino-protective group $R^3$.

The reaction of compounds of the formula (III) with 3-formamidopyridine to give compounds of the formula (IV) is carried out in organic or aqueous solvents at temperatures between 20° C. and 100° C., preferably between 60° C. and 80° C., with addition of a suitable salt catalyst.

Examples of suitable salt catalysts are NaBr, KI, KSCN, NaSCN, LiI.

A preferred organic solvent is dimethylformamide.

The reaction in aqueous solution using a large excess of KSCN is particularly preferred.

It is advantageous to employ a slight excess of 3-formamidopyridine, the addition of 1 equivalent of inorganic base, preferably sodium bicarbonate, being advantageous.

It is advantageous not to isolate the compounds of the formula (IV) but to convert them directly into the compound of the formula (I), after desalination with an adsorber resin. For this, the reaction solution obtained in the reaction (III)→(IV) is diluted with water and the mixture is then stirred with an adsorber resin, preferably HP 20. The adsorber resin is washed with water and the compound of the formula (IV) is then eluted from the resin by stirring the adsorber resin several times with a mixture of water and organic solvent, preferably with a water/acetonitrile mixture, preferably in the ratio 20:80 to 5:95. After the organic solvent has been stripped off in vacuo, an aqueous solution of the compound of the formula (III) is obtained.

The amine-protective group $R^3$ is split off enzymatically with immobilized penicillin G acylase at pH 7-8, preferably at pH 7.8, directly in the aqueous solution of the compound of the formula (IV). During the enzymatic cleavage, the pH value is kept constant by addition of a base, such as, for example, sodium hydroxide or triethylamine.

The title compound of the formula (I) is isolated as the crystalline hydrochloride directly from the aqueous cleavage solution by addition of concentrated hydrochloric acid and an organic solvent, preferably acetone.

Cephalosporins of the formula (II) ($R^2$=formyl) can be prepared from (I) by coupling with precursor acids, and compounds of the formula (II) ($R^2$=H) can be obtained from the products by splitting off the formyl group in a known manner.

EXAMPLE 1

7-Amino-3-(3-formamidopyridinium)methyl-3-cephem-4-carboxylate 32 g of 3-acetoxymethyl-7β-phenylacetamido-3-cephem-4-carboxylic acid and 6.8 g of sodium bicarbonate are dissolved in 32 ml of water. After addition of 144 g of potassium thiocyanate and 12.1 g of 3-formamidopyridine, the mixture is stirred at 65° for 4 hours. The reaction solution is diluted with 96 ml of water and the mixture is then stirred with 1,000 g of adsorber resin HP 20. The adsorber resin is filtered off with suction and washed 3× with 600 ml of water. The adsorber resin is then stirred 3× with 600 ml of acetonitrile/water 95:5 and filtered off with suction. The acetonitrile/water eluates are collected and the acetonitrile is stripped off in vacuo. The aqueous solution which remains (≈500 ml) is brought to pH 7.8 with 4 N triethylamine in ethanol, and 16 g of immobilized penicillin G acylase are added. The pH value is kept constant at 7.8 during the enzymatic cleavage. When the cleavage has ended, the enzyme-resin is filtered off, the filtrate is brought to pH 2 with concentrated hydrochloric acid and the precipitate formed is filtered off with suction over kieselguhr. The filtrate is added dropwise to 2 l of acetone, the desired product crystallizing out as the hydrochloride.

Yield: 13.7 g (×HCl×H₂O, 43%).

$^1$H—NMR (D₂O): δ(ppm)=9.53 (1H, s, H-2-Py); 8.70 (1H, d, J=7 Hz, H-6-Py); 8.43 (2H, m, H-4-Py, CHO); 8.01 (1H, dd, J=8 Hz, J=7 Hz, H-5-Py); 5.65

(1H, d, J=14 Hz, CH₂—Py); 5.35 (1H, d, J=14 Hz, CH₂—Py); 5.30 (1H, d, J=5 Hz, H-7-lactam); 5.19 (1H, d, J=5 Hz, H-6-lactam); and 3.71 (1H, d, J=18 Hz, S—CH₂).

EXAMPLE 2

7β-[(Z)-2-(2-Aminothiazol-4-yl)-2-methoxyiminoacetamido]-3-(3-formamidopyridinium)methyl-3-cephem-4-carboxylate 710 mg (3.58 mmole) (Z)-2-(2-aminothiazol-4-yl)-2-methoxyiminoacetic acid are dissolved in 4.5 ml of absolute dimethylformamide at room temperature, under nitrogen. After addition of 230 μl of tripropylamine and 310 μl of tributylamine, the mixture is cooled to −50° C. 290 μl of methyl chloride are added and the solution is rapidly added to a solution, cooled to 0° C., of 963 mg (2.6 mmol) of 7-amino-3-(3-formamidopyridinium)-methyl-3-cephem-4-carboxylate (×HCl) in 1.4 ml of water and 1.4 ml of triethylamine in the course of 30 minutes. After 5 minutes, the reaction solution is poured onto 400 ml of acetone. The precipitate is filtered off with suction, dried and chromatographed over adsorber resin HP 20 (eluent: acetonitrile/water 5:95).

Yield: 700 mg (52%).

¹H(DMSO—d₆): δ(ppm)=9.67 (1H, s, H-2-Py); 9.58 (1H, d, J=9 Hz, NH); 9.24 (1H, d, J=7 Hz, H-6-Py); 8.74 (1H, d, J=8 Hz, H-4-Py); 8.54 (1H, s, CHO); 8.13 (1H, m, H-5-Py); 7.24 (2H, bs, NH₂); 6.72 (1H, s, thiazole); 5.73 (1H, d, J-14 Hz, CH₂—Py); 5.68 (1H, dd, J=9 Hz, J=5 Hz, H-7-lactam); 5.24 (1H, d, J=14 Hz, CH₂—Py); 5.09 (1H, d, J=5 Hz, H-6-lactam); 3.80 (3H, s, OCH₃); 3.55 (1H, d, J=18 Hz, S—CH₂); and 3.15 (1H, d, J=18 Hz, S—CH₂).

EXAMPLE 3

7β-[(Z)-2-(2-aminothiazol-4-yl)-2-methoxyiminoacetamido]-3-(3-aminopyridinium)methyl-3-cephem-4-carboxylate 520 mg (1 mmole) of 7β-[(Z)-2-(2-aminothiazol-4-yl)-2-methoxyiminoacetamido]-3-(3-formamidopyridinium)methyl-3-cephem-4-carboxylate are suspended in 6 ml of methanol and dissolved by adding 0.4 ml of concentrated hydrochloric acid. After 5 hours, the methanol is stripped off in vacuo and the residue is taken up in 20 ml of water. The mixture id neutralized with ion exchanger MP 62 and then freeze-dried.

Yield: 350 mg (71.).

¹H—NMR (DMSO—d₆): δ(ppm)=9.51 (1H, d, J=9 Hz, NH); 8.52 (1H, s, H-2-Py); 8.44 (1H, d, J=7 Hz, H-6-Py); 7.71 (1H, dd, J=7 Hz, J=8 Hz, H-5-Py); 7.63 (1H, d, J=8 Hz, H-4-Py); 7.26 (2H, bs, NH₂); 6.83 (2H, bs, NH₂); 6.72 (1H, s, thiazole); 5.62 (1H, dd, J-9 Hz, J=5 Hz, H-7-lactam); 5.60 (1H, d, J=13 Hz, CH₂—Py); 5.09 (1H, d, J=5 Hz); 5.08 (1H, d, J=13 Hz, CH₂—Py); 3.81 (3H, s, OCH₃); 3.53 (1H, d, J=18 Hz, S—CH₂); and 3.07 (1H, d, J=18 Hz, S—CH₂).

It is understood that the specification and examples are illustrative but not limitative of the present invention and that other embodiments within the spirit and scope of the invention will suggest themselves to those skilled in the art.

I claim:

1. A process for the preparation of 7-amino-3-(3-formamidopyridinium)methyl-3-cephem-4-carboxylate of the formula

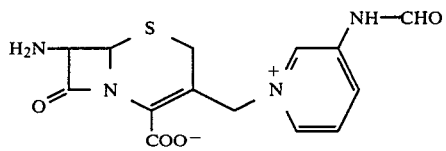

comprising (a) reacting a compound of the formula

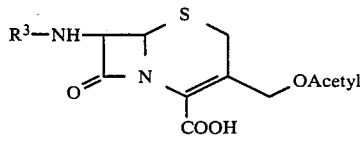

in which
R³ is a phenacetyl or a thienylacetyl group,
with a slight excess of 3-formamidopyridine to give the compound of the formula

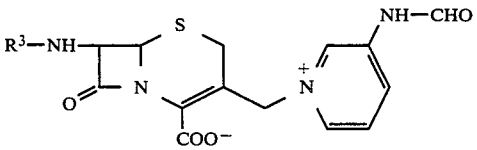

wherein said reaction is carried out in dimethylformanide at temperatures between 60° to 80° in the presence of NaBr, KI, KSCN, NaSCN or LiI, and (b) splitting off the R³ radical enzymatically with immobilized amino-protective penicillin G acylase at pH 7-8.

2. In the preparation of a cephalosporin by forming a 7-amino-3-(3-pyridinium)-methyl-3-cephem-4-carboxylate and forming an amide in the 7-position by linkage to an appropriate acid, the improvement which comprises forming the 7-amino-3-(3-pyridinium)-methyl-3-cephem-4-carboxylate by (a) reacting a compound of the formula

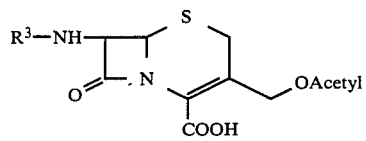

in which
R³ is a phenacetyl or a thienylacetyl group,
with a slight excess of 3-formamidopyridine to give the compound of the formula

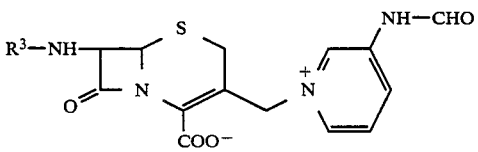

wherein said reaction is carried out in dimethylformamide at temperatures between 60° to 80° C. in the presence of NaBr, KI, KSCN, NaSCN or LiI and (b) splitting off the amino-protective R³ radical enzymatically with immobilized penicillin G acylase at pH 7-8.

3. The process according to claim 2, including the further step of removing the formyl radical.

4. The process according to claim 1, wherein the compound obtained in reaction (a) is not isolated and the enzymatic splitting of the $R^3$ radical of step (b) is carried out after desalination of the step (a) reaction solution with an absorber resin.

5. The process according to claim 2, wherein the compound obtained in reaction (a) is not isolated and the enzymatic splitting if the $R^2$ radical of step (b) is carried out after desalination of the step (a) reaction solution with an absorber resin.

* * * * *